(12) United States Patent
Baughman

(10) Patent No.: US 6,708,841 B2
(45) Date of Patent: Mar. 23, 2004

(54) GLOVE DISPENSER

(75) Inventor: Steven W. Baughman, Reynoldsburg, OH (US)

(73) Assignee: Safety Today, Inc., Groveport, OH (US)

( * ) Notice: Subject to any disclaimer, the term of this patent is extended or adjusted under 35 U.S.C. 154(b) by 59 days.

(21) Appl. No.: 10/025,151

(22) Filed: Dec. 20, 2001

(65) Prior Publication Data

US 2003/0116580 A1 Jun. 26, 2003

(51) Int. Cl.⁷ .............................. A47K 10/24
(52) U.S. Cl. .................. 221/46; 221/61; 221/155; 221/197; 221/281
(58) Field of Search .................. 221/45, 46, 61, 221/155, 197, 281, 286, 285, 287; 211/59.2; 312/35, 42, 34.4, 185, 188, 193, 246, 247, 293.2, 293.3

(56) References Cited

U.S. PATENT DOCUMENTS

| | | | |
|---|---|---|---|
| 760,113 A | * | 5/1904 | Friend |
| D299,686 S | | 2/1989 | Jonas |
| 4,938,382 A | * | 7/1990 | Frazier et al. ............... 221/45 |
| 4,942,992 A | | 7/1990 | Fischer |
| 4,993,589 A | | 2/1991 | McLaughlin |
| 4,997,105 A | | 3/1991 | Fischer |
| 5,088,620 A | | 2/1992 | Kelliher |
| 5,096,089 A | | 3/1992 | McLaughlin |
| D375,010 S | | 10/1996 | Karnes |
| 5,570,808 A | | 11/1996 | Tassoni |
| 5,642,837 A | * | 7/1997 | Hayes et al. ............... 221/197 |
| D387,981 S | | 12/1997 | Mosior |
| 5,695,065 A | | 12/1997 | Kennedy |
| 5,816,440 A | | 10/1998 | Shields |
| 5,878,909 A | | 3/1999 | Rogow |
| 5,884,805 A | * | 3/1999 | Tramontina ............... 221/45 |
| 5,921,434 A | | 7/1999 | Hollander |
| 5,927,543 A | | 7/1999 | Dejardin |
| D415,914 S | | 11/1999 | Shields |
| 6,021,919 A | * | 2/2000 | Kelly ............... 221/155 X |
| 6,062,421 A | | 5/2000 | Marley |
| 6,230,929 B1 | * | 5/2001 | Phelps et al. ............... 221/46 |
| 6,520,372 B2 | * | 2/2003 | Phelps ............... 221/45 X |

\* cited by examiner

*Primary Examiner*—David H. Bollinger
(74) *Attorney, Agent, or Firm*—TechnoProp Colton LLC

(57) ABSTRACT

Glove dispenser having a back plate, a cover, a angled rack for securing a pre-packaged box of gloves within the device at an angle with respect to the back plate, and an aperture in the cover through which gloves can be dispensed at an ergonomic angle.

38 Claims, 7 Drawing Sheets

GLOVE DISPENSER

BACKGROUND OF THE INVENTION

1. Technical Field

The present invention relates generally to the field of glove dispensers and more specifically to easily loadable, wall- or surface-mountable glove dispensers for boxes of pre-packaged gloves, including vinyl, latex and polyethylene gloves and other protective gloves, which can store and dispense such gloves in an ergonomic manner.

2. Prior Art

Glove dispensers are currently found in almost every area where gloves are present such as medical facilities (hospitals, physicians, dentists, EMS, etc.), industrial first aid stations, food service areas, schools, police and fire departments, high-tech clean rooms, beauty salons, homes, postal facilities, and anywhere disposable gloves are needed. Further, because of the increasing seriousness of present day diseases and increases in the number of events of bioterrorism, protective gloves such as surgical gloves are going to be dispensed in more areas and in more facilities.

The main advantages of glove dispensers is that they ensure that gloves can be found in a designated place, can be retrieved conveniently, and are at least somewhat protected from contaminants. Such dispensers can allow people to find gloves without fumbling and are especially helpful when time is critical. Further, glove dispensers are useful as an organizational tool to save counter space and make a work area look more professional.

U.S. Pat. No. 4,993,589 to McLaughlin discloses a dispensing apparatus for disposable gloves that allows users to retrieve gloves one at a time in a relatively simple manner. The gloves are loaded through a top opening and dispensed through a forward opening. Because McLaughlin '589 discloses a device that incorporates a spring means to generally dispense gloves forward, the user must user an unnatural forward movement to retrieve the gloves from the dispensing apparatus and is not ergonomic.

U.S. Pat. No. 5,096,089 to McLaughlin discloses a dispenser for disposable gloves that comprises a generally rectangle enclosure for housing gloves. The gloves that are dispensed by the device in McLaughlin '089 are a stack of gloves attached to each other at the wrist area. A mounting strip extends across the upper wrist portion of the stack of gloves and is fixed to each glove above a tear line. Because McLaughlin '089 discloses an apparatus that generally dispenses gloves downward, the user must use an unnatural downward movement to retrieve the gloves and is not ergonomic. Further, the McLaughlin '089 device is useful only for the pre-mounted stack of gloves.

U.S. Pat. No. 5,570,808 to Tassoni discloses a dispenser comprising multiple units for protective gloves that has at least one compartment for holding a bulk quantity of gloves. Tassoni '808 discloses a dispenser that must be filled with individual gloves and does not accommodate boxes of prepackaged gloves, thus subjecting the gloves to additional, possibly detrimental, handling of the gloves. Further, this apparatus requires that the user retrieve gloves using an upward movement, which is not ergonomic.

U.S. Pat. No. 5,927,543 to Dejardin et al. discloses a dispenser for gloves made of sheet material and comprises a box that defines a volume for a pre-determined number of the gloves. This apparatus does not accommodate boxes of gloves and requires an unnatural downward movement to retrieve gloves, which is not ergonomic.

Notwithstanding the prior art, there is need for an easily loadable, wall-mountable, glove dispenser that can accommodate at least one box of prepackaged gloves, such as, but not limited to, vinyl gloves, latex gloves, and polyethylene gloves, which can store and dispense such gloves in an ergonomic manner. There further is a need for a device to dispense gloves without negative consequences such as a substantial contamination to the gloves. It is to such needs and others that the present invention is directed.

BRIEF SUMMARY OF THE INVENTION

Briefly, the present invention is an easily loadable, surface- or wall-mountable, glove dispenser for prepackaged gloves, especially pre-boxed gloves. The dispenser can store and dispense such gloves in an ergonomic manner, and is suitable for any type of glove, such as latex, vinyl and polyethylene. When in a closed configuration, the dispenser is a generally rectangular, box-shaped unit having a somewhat triangularly skewed side cross section and comprising a back plate and a cover with an aperture through which the gloves are retrieved. The device has an interior volume, encases at least one box of prepackaged gloves, and includes means for securing the box of prepackaged gloves within the device that allows for the angular dispensing of gloves in an ergonomic and efficient manner.

The dispenser is structured so as to contain at least one commercially available prepackaged box of disposable gloves. This allows the gloves to be placed in the device without actually touching the gloves, thus reducing the chance of contaminating the gloves. The dispenser comprises a means for securing the box of prepackaged glove box within the device that allows for the gloves to be dispensed at an angle (rather than only downward or forward), which allows a more natural movement of the hand and arm when obtaining a glove from the dispenser. The dispenser further comprises a rack structure comprising at least one protrusion for holding the box of prepackaged gloves, and therefore the gloves themselves, at the dispensing angle, and at least one segment for holding the box of gloves within the dispenser with respect to gravity.

Thus, it can be seen that one advantage of the present invention is a glove dispenser for easy, reliable, convenient, and ergonomic, one at a time, dispensing of gloves.

Another advantage of the present invention is that the angled means for holding the box of prepackaged gloves allows the gloves to be more easily dispensed without compromising other function of the dispenser.

Other advantages of the present invention include a glove dispenser that is easy to charge or recharge with gloves, and is capable of dispensing a wide variety of gloves (types, sizes and materials) in a convenient and reliable fashion.

The flexibility of the invention makes it useful and convenient to use in a wide variety of applications (such as ambulances, police cars, fire vehicles, hospital emergency rooms and labs, as well as in the offices of doctors and dentists) and protects the gloves against tampering, the elements of weather, and environmental contaminants. Further, because of these characteristics, and particularly because of the dispenser's simplicity, the present invention provides a glove dispenser that is of simple construction and inexpensive to manufacture.

These features, and other features and advantages of the present invention, will become more apparent to those of ordinary skill in the relevant art when the following detailed description of the preferred embodiments is read in conjunction with the appended drawings in which like reference numerals represent like components throughout the several views.

DETAILED DESCRIPTION OF THE PREFERRED EMBODIMENTS

Figure 1:
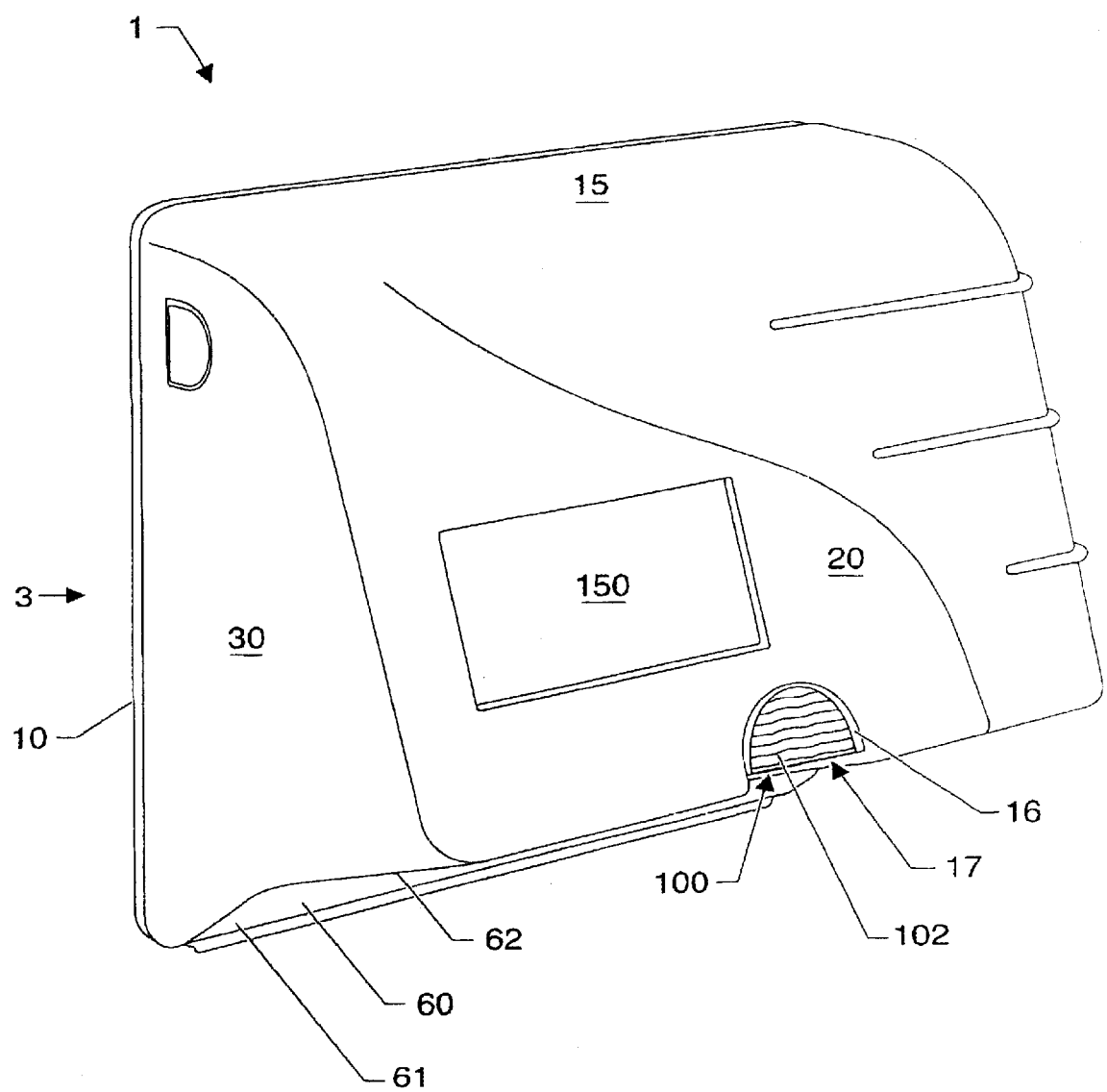
FIG. 1 is a perspective view of the glove dispenser in a closed configuration.
Figure 2:
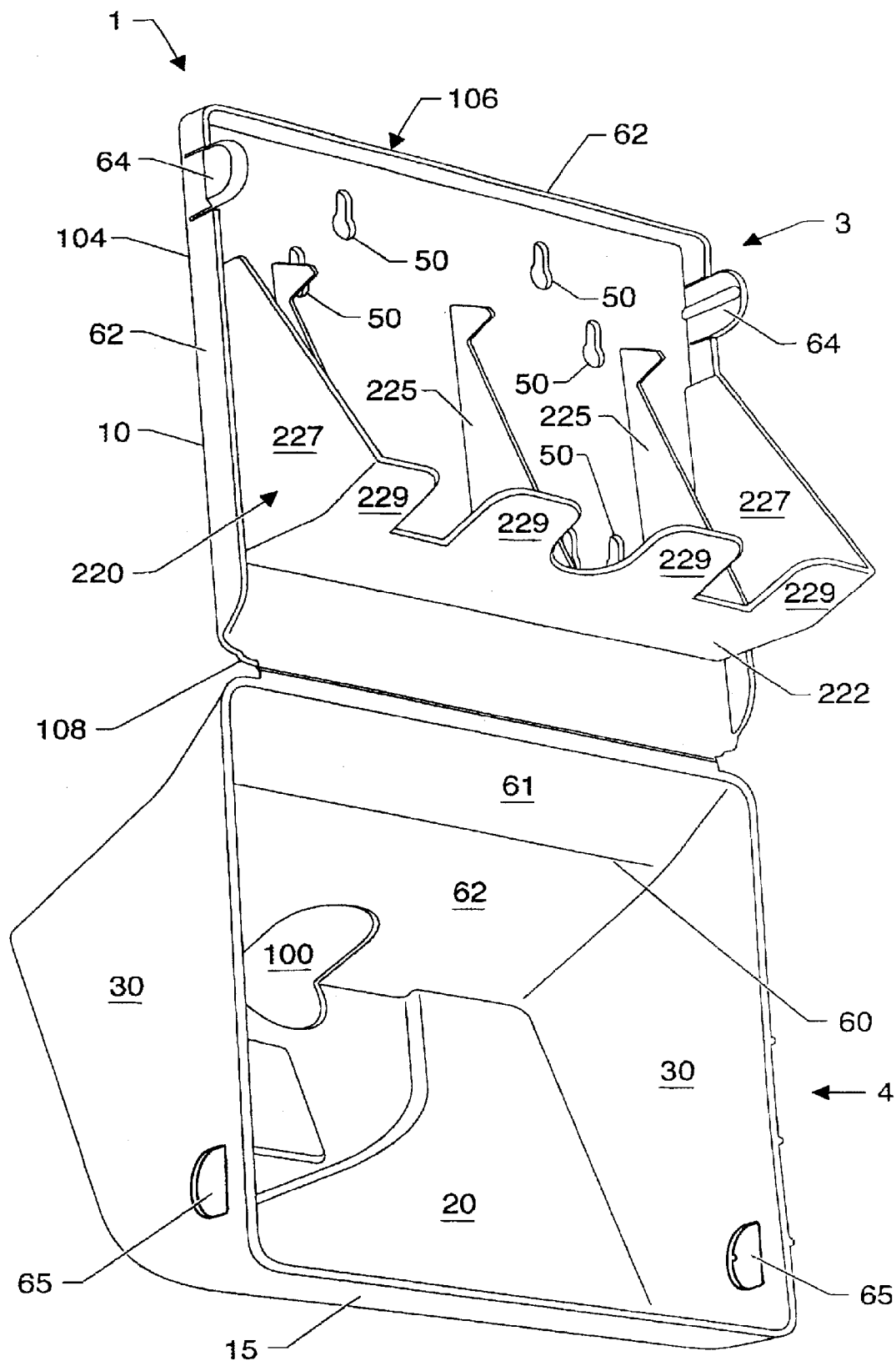
FIG. 2 is a perspective view of the glove dispenser in an opened configuration.
Figure 3:
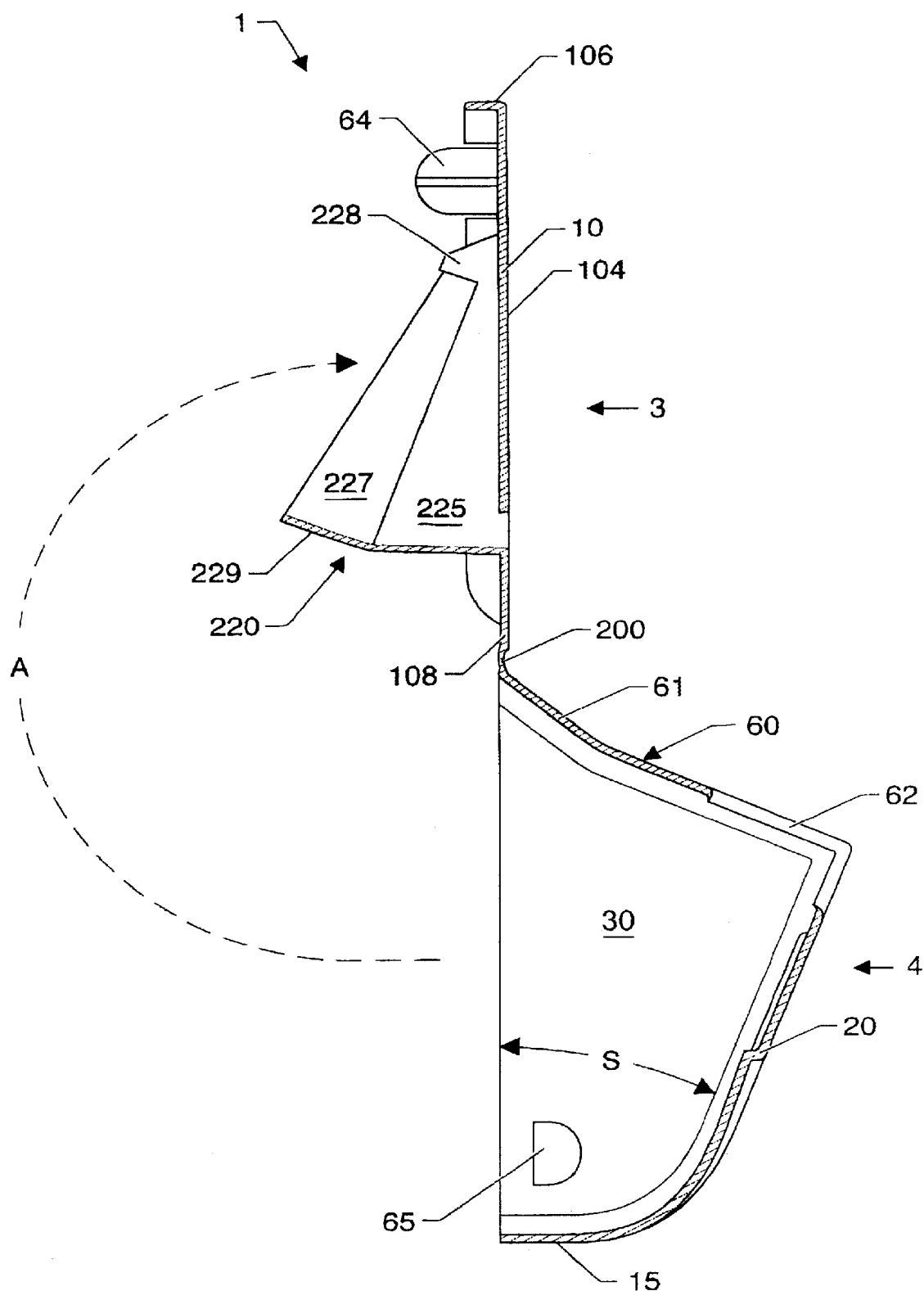
FIG. 3 is a side sectional view of the glove dispenser in an opened configuration.
Figure 4:
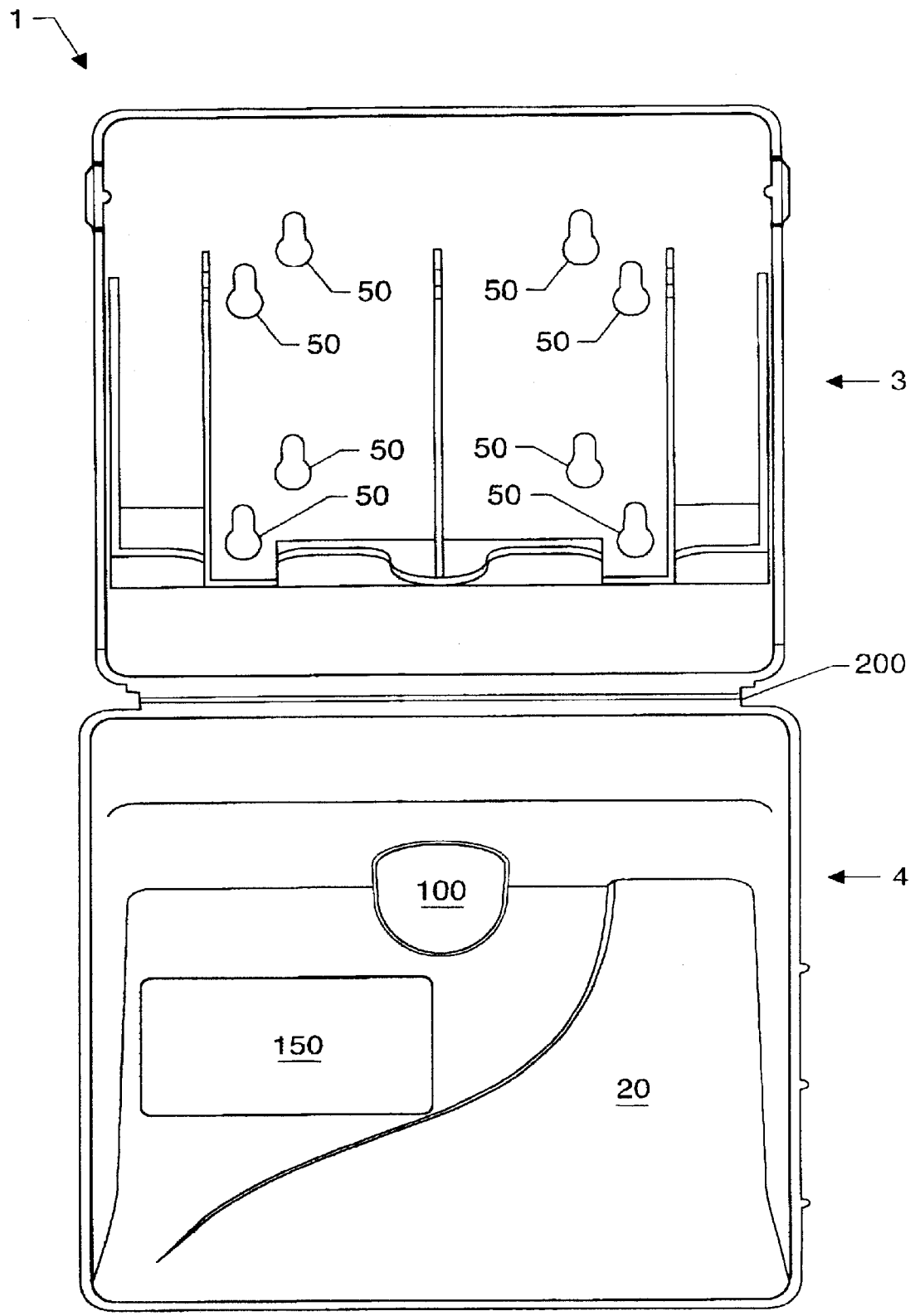
FIG. 4 is a front plan view of the glove dispenser in an opened configuration.
Figure 5:
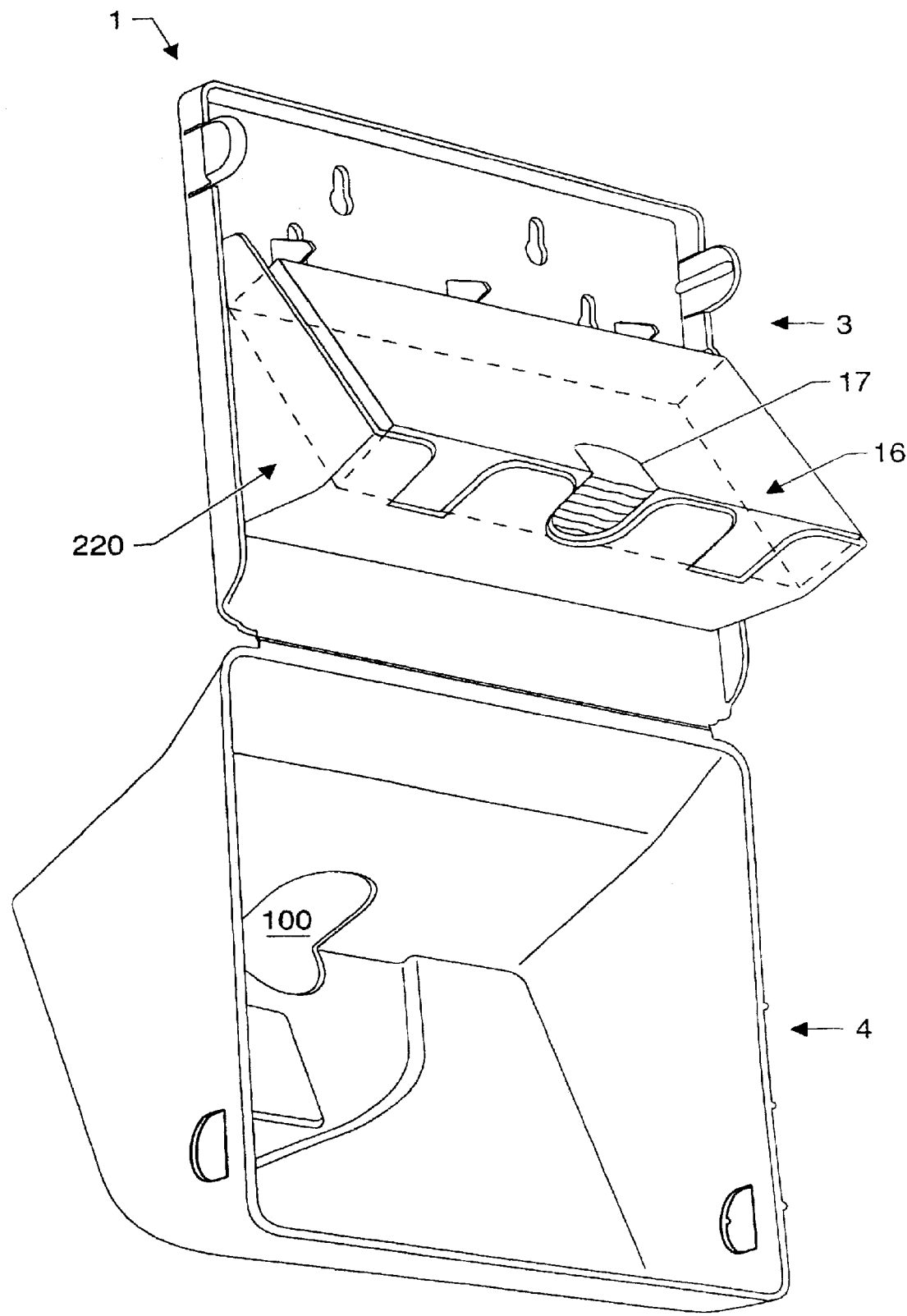
FIG. 5 is second perspective view of the glove dispenser in an opened configuration with an installed box of prepackaged gloves.
Figure 6:
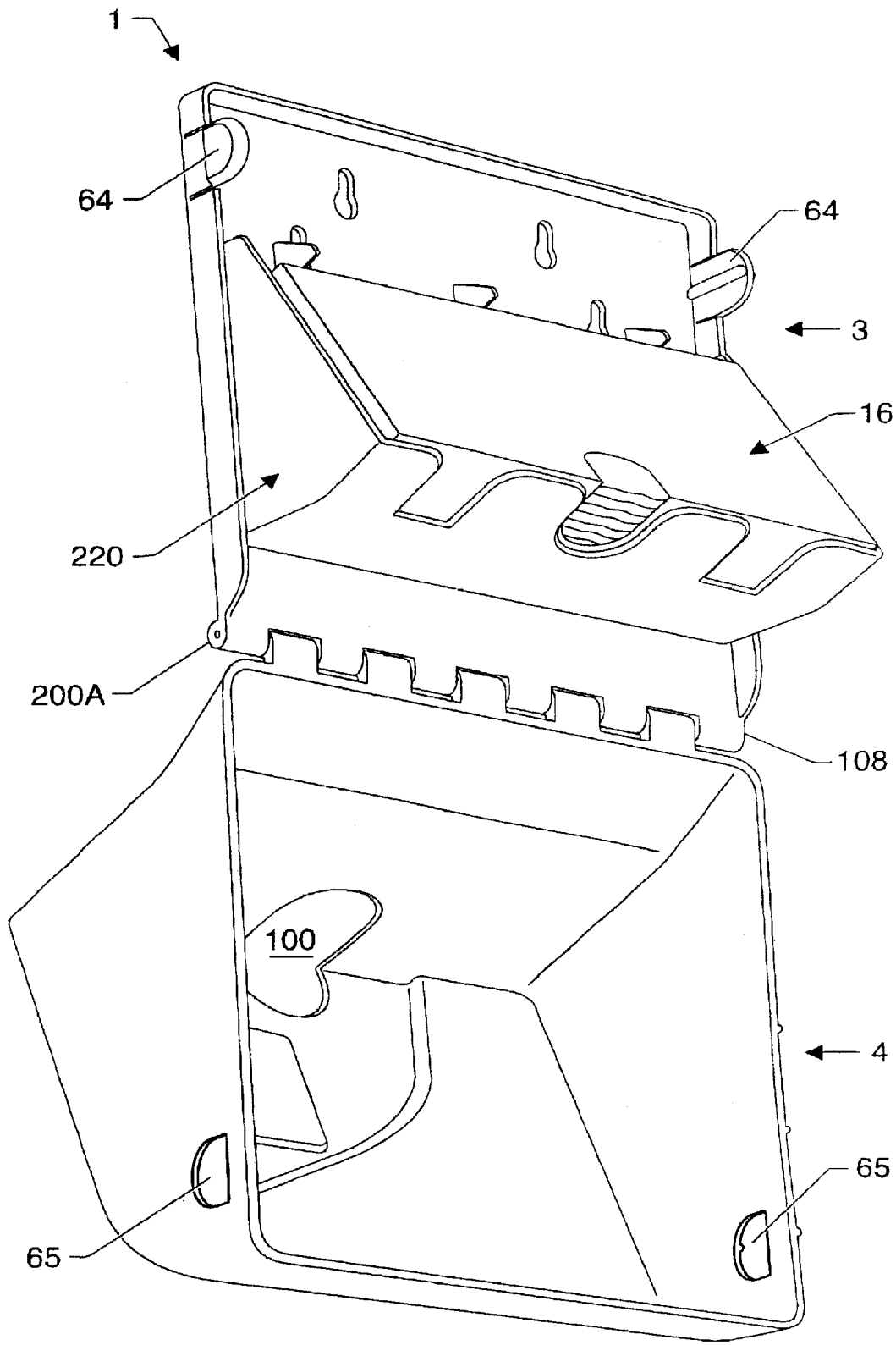
FIG. 6 is the second perspective view of the glove dispenser as shown in FIG. 5 with an alternate hinge arrangement.
Figure 7:
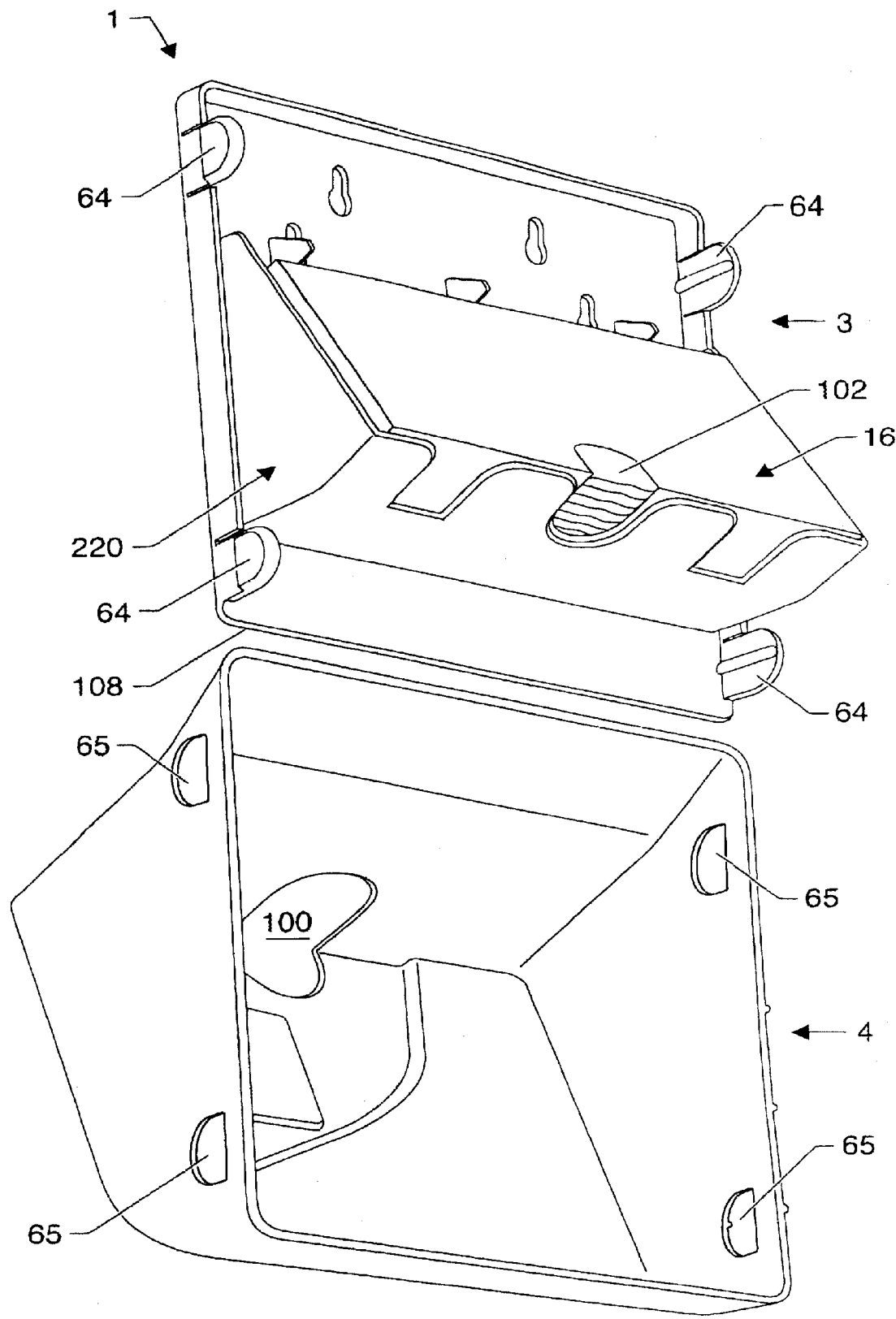
FIG. 7 is an alternative embodiment of the glove dispenser having a separate cover and back plate.

Referring now generally to FIGS. 1–7, preferred embodiments of the invention are shown. FIG. 1 is a perspective view of an embodiment of the glove dispenser 1 in a closed configuration that shows the embodiment as rigid enclosed volume. FIG. 2 is a perspective view of an embodiment of the glove dispenser 1 in an opened configuration that shows a holding means 225, 227, 228, 229 for retaining the prepackaged box 16 of gloves 102 and the general interior structure of a preferred embodiment. FIG. 3 is a side sectional view of an embodiment of the glove dispenser 1 in an opened configuration that shows a holding means 225, 227, 228, 229 for retaining the prepackaged box 16 of gloves 102 and one joint 200 for attaching the cover 4 to the back plate 3. FIG. 4 is a front plan view of an embodiment of the glove dispenser 1 in an opened configuration that shows the position of an aperture 100 for obtaining gloves from the dispenser 1 with respect to the cover 4. FIG. 5 is a perspective view of an embodiment of the glove dispenser 1 charged with a prepackaged box 16 of gloves 102. FIG. 6 shows an alternate hinge 200A arrangement between the cover 4 and the back plate 3. FIG. 7 shows an alternative embodiment of the glove dispenser 1 having a separate cover 4 and back plate 3.

The dispenser 1 can be manufactured relatively simply with inexpensive materials and conventional techniques. Preferably, the dispenser 1 is made from conventional polymer and/or metal materials, is easily manufactured using standard molding and/or forming techniques, and is fabricated in a relatively inexpensive manner. However, other types of suitable materials, such as woods, ceramics, fiber matrices, glasses or the like, which provide sufficient strength and resistance to ambient or weather elements for the intended application, may be used without departing from the scope of the present invention.

The preferred embodiments of the invention generally include dispensers 1 that have an opened configuration such as shown in FIG. 2 for loading and cleaning and a closed configuration such as shown in FIG. 1 for dispensing. In the closed configuration, dispenser 1 contains and holds prepackaged boxes 16 of gloves 102 and persons desiring to retrieve gloves 102 can use dispenser 1 for such purposes. In the opened configuration, dispenser 1 can be charged (that is, loaded or reloaded), if necessary, with at least one prepackaged box 16 of gloves 102.

Referring now to FIG. 1, one preferred embodiment of the glove dispenser 1, when in a closed configuration, is generally a triangularly skewed rectangular, box-shaped unit comprising back wall 10, front wall 20, sidewalls 30, top wall 15, and bottom wall 60 Preferably, bottom wall 60 comprises two intersecting plates 61 and 62, wherein the angle of intersection, measured from the outside of the device, between plates 61 and 62 is greater than 90 degrees but less than 180 degrees. Dispenser 1 in a closed configuration is essentially an enclosed space that has a volume sufficient to encase at least one prepackaged box 16 of gloves 102. Preferably, at the intersection of bottom wall 10 and front wall 20, there is aperture 100 through which gloves 102 are dispensed. The structure of dispenser 1 can have curved edges so as to prevent persons from becoming injured from contact with the corners of dispenser 1.

When dispenser 1 is an opened configuration as shown in FIG. 2, it is more apparent that the preferred embodiments can essentially comprise two components, namely back plate 3 and cover 4. Back plate 3 can comprise only back wall 10 of the dispenser 1, or preferably can comprise back wall 10, means for securing 225, 227, 228, 229 (discussed in more detail later) prepackaged box 16 of gloves 102 in dispenser 1, and means for attaching 50 (discussed in more detail later) dispenser 1 to a wall or other surface. Cover 4 generally comprises front wall 20, bottom wall 60, sidewalls 30, aperture 100, and optionally a window 150. In some embodiments, as shown in FIGS. 2–5, dispenser 1 is formed as a single structure comprising back plate 3 and cover 4. In other embodiments, as shown in FIGS. 6 and 7, dispenser 1 is formed by attaching together separate back plate 3 and cover 4 structures.

As shown in FIGS. 2 and 3, back plate 3 and cover 4 can be connected by means of a joint 200 along the bottom edge 108 of back plate 10 and bottom wall 60. In the embodiments where dispenser 1 is formed from a single piece of material, joint 200 can be constructed by any conventional forming means, such as a narrowing or thinning of the material of manufacture between back plate 3 and bottom wall 60, or any other means understood by persons of ordinary skill in the art to form such a joint 200 or a hinge. As shown in FIG. 6, in the embodiments where dispenser 1 is formed from a separate back plate 3 and cover 4, joint 200A can be formed from a pin and hole structure similar to a conventional door hinge. Alternatively, as shown in FIG. 7, in other embodiments where dispenser 1 is formed from a separate back plate 3 and cover 4, back plate 3 and cover 4 can be simply connected (or snapped) together without the aid of a joint 200. FIG. 7 shows an alternative embodiment comprising a separate cover 4 and back plate 3 that are held together by additional latches 64 and apertures 65, as disclosed in more detail below.

Referring now to FIGS. 2 and 3, back plate 3 and cover 4 can be secured or reversibly secured together by means of latches 64 cooperating with locking apertures 65, and/or engaging lips 62. Preferably, cover 4 comprises one or more extended latches 64 at the upper side edge 104 of back plate 10 that can reversibly engage locking apertures 65 in cover 4. Side edge 104 of back plate 10, as well as upper edge 106 of back plate 3, can have at least one perpendicularly extending engaging lip 62 for more support. In the embodiment shown in FIG. 2, lip 62 extends about the periphery of back plate 3 along both side edges 104 and top edge 106, but not along bottom edge 108. Lip 62 may extend on any, all, or any combination of, or portions of, edges 104, 106, 108.

In the preferred embodiments where dispenser 1 comprises a joint 200 between back plate 3 and cover 4, cover 4 is pivotally swung upward about joint 200, represented by arrow A on FIG. 3, and secured by latches 64 engaging locking apertures 65. Latches 64 are bendable or flexible extensions extending from back plate 3 and comprise portions that fit within locking apertures 65, thus holding cover 4 to back plate 3. Further, to release cover 4 from back plate 3, the user can apply inward pressure to latches 64, thus disengaging latches 64 from locking apertures 65, and swing cover 4 downward about joint 200.

There are alternative means for securing back plate 3 and cover 4 together. Alternative means include hinges without the presences of latches. Alternatively, as shown in one embodiment in FIG. 7, if joint 200 is not present, back plate 3 and cover 4 can be snapped together and secured by a plurality of latches 64 or further by engaging lips 62.

Referring now to FIG. 4, back plate 3 can have means for securing back plate 3 to a wall or other surface, which thereby secures dispenser 1 to the surface. For example such means for securing back plate 3 to a wall or other surface can include keyholes 50, whereby mounted posts (not shown) attached to the surface are inserted into keyholes 50 to secure dispenser 1 in place. Alternatively, back plate 3 can be secured to a surface by means of security screws mounted through one or more of keyholes 50. Alternatively, dispenser 1 may be mounted to a surface by means of a wall bracket in which dispenser 1 is removably fitted, by an adhesive, or by other conventional means.

Dispenser 1 can be mounted in any position that allows for the securing of back plate 3 to a surface. Preferably, dispenser 1 is mounted vertically, that is, with bottom edge 108 closest to the ground, side edges 104 vertical, and top edge 106 farthest from the ground, so to allow the user to manually pull a glove 102 out of aperture 100 more ergonomically. Further in a vertical position, gloves 102 flow with the force of gravity, which further facilitates the dispensing of gloves 102 and helps ensures that the last glove 102 in the prepackaged box 16 is available for retrieval.

Referring back to FIG. 2, the interior of a preferred embodiment of dispenser 1 is shown in more detail. Back plate 3 preferably comprises structural means or rack 220 to support and angle prepackaged box 16 of gloves 102 within dispenser 1. Rack 220 comprises back supports 225, side guides 227, top stays 228, and bottom supports 229. Side guides 227 are protrusions having a vertical orientation and extend generally horizontally outwardly from back plate 3 and are located proximal to the side edges 104 of back plate 3. Preferably there are two side guides 227, but one can suffice. Bottom supports 229 extend generally horizontally outwardly and upwardly from back plate 3 and are located beneath back supports 225 and between side guides 227, if there are two side guides 227, or inwardly toward the center of back plate 3 from side guide 227, if there is one side guide 227. Spacer plate 222 is a generally horizontal rectangular structure extending from back plate 3 between the bottom edges of side guides 227 and forming a squared-off "U" shape with side guides 227. As disclosed in more detail later, a purpose of spacer plate 222 is to arrange bottom supports in a location so as to allow prepackaged box 16 of gloves 102 to sit at an angle within dispenser 1, as shown in FIG. 5.

Back supports 225 also are protrusions having a vertical orientation and extend generally horizontally outwardly from back plate 3 and are located between side guides 227, if there are two side guides 227, or inwardly toward the center of back plate 3 from side guide 227, if there is one side guide 227. Preferably there are two or more back supports 225, with three being shown in FIG. 2, but one can suffice. Bottom supports 229 are protrusions from spacer plate 222 and have a generally horizontal orientation angled slightly upward relative to back plate 3 and spacer plate 222 toward the front of dispenser 1.

As can be seen in FIGS. 2 and 3, side guides 227 have a generally triangular shape with an apex angle a selected to correspond with the angled slope S of cover 4. As discussed below, this angle allows cover 4 to close easily over rack 220 and for prepackaged box 16 to be held securely between the inner surface of cover 4 and back supports 225. As shown in more detail in FIG. 5, prepackaged box 16 fits between and is held in a generally horizontal configuration within rack 220 by side guides 227.

Back supports 225 also have a generally triangular shape with an apex angle $\theta$ selected to correspond to the desired ergonomic angle for supporting box 16 and allowing the angled removal of gloves 102 from dispenser 1. Back supports 225 do not protrude from back plate 3 as far as side guides 227 so as to allow side guides 227 to hold box 16 within dispenser 1. As shown in more detail in FIG. 5, prepackaged box 16 is supported by and is held in an angled ($\Theta$) configuration within rack 220 by back supports 225 between side guides 227.

Bottom supports 229 can be of any shape so long as they are wide enough to support box 16 within dispenser 1. In FIG. 2, bottom supports 229 are shown as a collection of squares having rounded edges. Top stays 228 can be extensions of back supports 225 or separate extensions from back plate 3. In either structure, top stays 228 cooperate with bottom supports 229 to maintain box 16 in a generally horizontal configuration within rack 220. Angles a and $\theta$ can be the same or different.

Now referring back to FIGS. 1 and 4, at least one dispensing aperture 100 is formed at the the junction of front wall 20 and bottom wall 60 allowing access to gloves 102 within prepackaged box 16 within dispenser 1. The user grasps glove 102 through aperture 100 to facilitate removal of glove 102 through aperture 100. Preferably, aperture 100 can be formed by U-shaped openings in walls 20 and 60 in cover 4 and is large enough to allow gloves 102 to flow out of dispenser 1 without undue obstruction. Aperture 100 is formed through cover 4 to coincide and line up with an opening 17 in prepackaged box 16.

Referring now to FIG. 5, rack 220 for securing prepackaged box 16 of gloves 102 within dispenser 1 allows for gloves 102 to be dispensed at an angle $\Theta$ (rather than directly downward or forward) with respect to back wall 3. Rack 220 preferably is structured to hold prepackaged box 16 such that gloves 102 are dispensed at angle between 90 degrees and 180 degrees on a common Cartesian coordinate system, with the positive X-axis pointing vertically upwards from the ground and the positive Y-axis pointing horizontally outwards parallel to the ground from back plate 3 towards cover 4 of dispenser 1. Preferably, rack 220 can hold prepackaged box 16 at an angle such that gloves 102 are dispensed at an angle between 95 and 175 degrees using the above-defined coordinate system. Most preferably, rack 220 can hold prepackaged box 16 at an angle allowing the most ergonomically advantageous dispensing of gloves 102 from dispenser 1. It is understood to those of ordinary skill that the optimal angle to secure prepackaged box 16 within dispenser 1 for optimal dispensing can depend on the size and shape of prepackaged box 16 and can be determined without undue experimentation.

One advantage of having an angled rack 220 is that such a structure allows gloves 102 to be more easily dispensed without compromising the other functions of dispenser 1.

Preferred embodiments can allow the user to retrieve gloves 102 by pulling each glove 102 from a multitude of directions, including forward, downwards, and at an angle between forwards and downwards. Preferably, the user applies a force to retrieve glove 102 at angle between 95 degrees and 175 degrees using the above-defined coordinate system. The human arm tends to be most comfortable pulling at an angle of between about 125 degrees and 155 degrees using the above-defined coordinate system. By structuring dispenser 1 with these angles, a person may more ergonomically grasp one glove 102 with a motion more natural to the user and without having to lean underneath dispenser 1. This ergonomic advantage arises out of the novel angled dispensing mechanism. Further, because of the angled mechanism, gloves 102 flow more easily out of the prepackaged box 16 and allow for more efficiency.

When prepackaged box 16 of gloves 102 is installed in dispenser 1, opening 17 in box 16 lines up with aperture 100. It is preferred that rack 220 be constructed in a manner that aligns opening 17 with aperture 100 so as to allow for the most efficient dispensing of gloves 102. As would be known to those of ordinary skill in the art, the placement of aperture 100 on cover 4 should be coordinated with opening 17, and can be varied upon manufacture to accommodate various different sizes, shapes and structures of prepackaged boxes 16.

The present invention can be used to dispense an array of types of gloves 102 that can vary in size, shape and material. Preferably, dispenser 1 is charged with a prepackaged box 16 of prepackaged vinyl, latex or polyethylene gloves 102, because these types of gloves 102 are used widely used and commercially available. It is contemplated that dispenser 1 can be manufactured in different sizes and with aperture 100 in different places for use with any type of glove 102 available and with any type of prepackaged box 16 having an opening 17.

To charge or recharge dispenser 1 with a fresh prepackaged box 16 of gloves 102, the user simply removes cover 4 from the back plate 3 (either by pivoting cover 4 downwards about joint 200 if dispenser 1 is of unitary construction or by removing cover 4 from back plate 3 if dispenser 1 is of multi-component construction) and positions prepackaged box 16 on rack 220. After placing prepackaged box 16 on rack 220, the user secures cover 4 on back plate 3 and continues to use dispenser 1. Once dispenser 1 is charged with a prepackaged box 16 of gloves 102, a user can conveniently and ergonomically retrieve one glove 102 at a time by grasping and pulling on the outermost glove 102 through aperture 100 and opening 17. The amount of force required to retrieve a glove 102 can be minimal based on the ergonomic angle θ. When the prepackaged box 16 is exhausted, dispenser 1 can be recharged with a fresh new prepackaged box 16 of gloves 102.

The above detailed description of the preferred embodiments, and the appended figures are for illustrative purposes only and are not intended to limit the scope and spirit of the invention, and its equivalents, as defined by the claims. One skilled in the art will recognize that many variations can be made to the invention disclosed in this specification without departing from the scope and spirit of the invention.

What is claimed is:

1. A glove dispenser comprising:
   a. back plate;
   b. cover comprising front wall, sidewalls, bottom wall and top wall, wherein the cover fits upon the back plate to create a holding structure with an interior volume for containing a prepackaged box of gloves;
   c. means for holding the prepackage box of gloves within the dispenser at a selected angle that is neither parallel nor perpendicular to the back plate; and
   d. aperture in the cover through which the gloves can be dispensed.

2. The glove dispenser as claimed in claim 1, wherein the cover is pivotally connected to the back plate.

3. The glove dispenser as claimed in claim 1, wherein the cover is removably attached to the back plate.

4. A glove dispenser as claimed in claim 1, wherein the means for holding the prepackaged box of gloves is attached to the back plate at angle between 1 and 89 degrees from horizontal upward with respect to gravity and outward with respect to the back plate.

5. The glove dispenser as claimed in claim 4, wherein the means for holding the prepackaged box of gloves on the back plate is angled between 30 and 60 degrees from horizontal upward with respect to gravity and outward with respect to the back plate.

6. The glove dispenser as claimed in claim 4, wherein the angle between forward and downward is between 10 degrees and 60 degrees.

7. A glove dispenser comprising:
   a. a back plate;
   b. a cover with a front wall, sidewalls, a bottom wall and a top wall, wherein the cover fits upon the back plate to create a holding structure with an interior volume for containing a prepackaged box of gloves;
   c. an angled rack for holding the prepackaged box of gloves on the back plate at and angle with respect to the back plate, wherein the angle is between perpendicular to and parallel with the back plate;
   d. an aperture in the cover through which gloves can be dispensed.

8. The glove dispenser as claimed in claim 7, wherein the cover is pivotally connected to the back plate.

9. The glove dispenser as claimed in claim 7, wherein the cover is releasably secured to the back plate.

10. The glove dispenser as claimed in claim 9, further comprising a window in the cover.

11. The glove dispenser as claimed in claim 10, wherein the means for holding the prepackaged box of gloves on the back plate is angled between 1 and 89 degrees from vertical with respect to the back plate.

12. The glove dispenser as claimed in claim 11, wherein the angled rack for holding the prepackaged box of gloves box on the back plate is angled between 10 and 20 degrees from vertical with respect to the back plate.

13. A glove dispenser of the type comprising a container having an interior volume into which a prepackaged box of disposable gloves is secured and having an opening through which gloves may be dispensed, comprising:
   a. a back plate for securing the dispenser onto a surface;
   b. an angled rack attached to the back plate for holding the prepackaged box of gloves within the dispenser at a selected angle that is neither parallel to not perpendicular to the back plate; and
   c. a cover that is releasably attached to the back plate and is movable between an open position and a closed position relative to the back plate so as to allow access to the interior volume of the dispenser.

14. The glove dispenser as claimed in claim 13, wherein the angled rack comprises supports for holding the prepackaged box of gloves at the selected angle.

15. The glove dispenser as claimed in claim 14, wherein the cover comprises a front wall comprising a bottom edge and a bottom wall comprising a front edge that intersect at a junction, and the opening through which gloves may be dispensed is located at the junction.

16. The glove dispenser as claimed in claim 15, wherein a first portion of the opening through which gloves may be dispensed is through the front wall and a second portion of the opening through which gloves may be dispensed is through the bottom wall.

17. The glove dispenser as claimed in claim 16, wherein the front wall slopes outwardly away from the back plate in a direction from the top of the back plate to the bottom wall.

18. The glove dispenser as claimed in claim 17, wherein the cover is hingedly attached to the back plate.

19. The glove dispenser as claimed in claim 17, wherein the cover is releasably attached to the back plate.

20. The glove dispenser as claimed in claim 17, wherein the front wall further comprises a window for viewing into the interior volume of the dispenser.

21. The glove dispenser as claimed in claim 17, wherein the back plate is mountable to a vertical surface, the angled rack supports the prepackaged box of gloves at an angle that is neither parallel to not perpendicular to the vertical surface, and the opening through which gloves may be dispensed faces in a forward and downward direction relative to and away from the vertical surface.

22. A glove dispenser of the type comprising a container having an interior volume into which a prepackaged box of disposable gloves is secured and having an opening through which gloves may be dispensed, comprising:
   a. a back plate for securing the dispenser onto a vertical surface;
   b. an angled rack attached to the back plate for holding the prepackaged box of gloves within the dispenser at a selected angle that is neither parallel to not perpendicular to the back plate and to the vertical surface; and
   c. a cover that is releasably attached to the back plate and is movable between an open position and a closed position relative to the back plate so as to allow access to the interior volume of the dispenser,
      wherein at least a portion of the opening through which the gloves may be dispensed is located through the cover and the opening through which gloves may be dispensed faces in a forward and downward direction relative to and away from the vertical surface.

23. The glove dispenser as claimed in claim 22, wherein the angled rack comprises supports for holding the prepackaged box of gloves at the selected angle.

24. The glove dispenser as claimed in claim 22, wherein the cover further comprises a front wall comprising a bottom edge and a bottom wall comprising a front edge that intersect at a junction, and the opening through which gloves may be dispensed is located at the junction.

25. The glove dispenser as claimed in claim 24, wherein a first portion of the opening through which gloves may be dispensed is through the front wall and a second portion of the opening through which gloves may be dispensed is through the bottom wall.

26. The glove dispenser as claimed in claim 24, wherein the front wall slopes outwardly away from the back plate in a direction from the top of the back plate to the bottom wall.

27. The glove dispenser as claimed in claims 22, wherein the cover is hingedly attached to the back plate.

28. The glove dispenser as claimed in claim 22, wherein the cover is releasably attached to the back plate.

29. The glove dispenser as claimed in claim 22, wherein the front wall further comprises a window for viewing into the interior volume of the dispenser.

30. A glove dispenser of the type comprising a container having an interior volume into which a prepackaged box of disposable gloves is secured and having an opening through which gloves may be dispensed, comprising:
   a. a back plate for securing the dispenser onto a vertical surface and comprising a top edge and a bottom edge;
   b. an angled rack attached to the back plate for holding the prepackaged box of gloves within the dispenser at a selected angle that is neither parallel to not perpendicular to the back plate and to the vertical surface and comprising a top portion, a central portion and a bottom portion, wherein the top portion is proximal to the top edge of the back plate and the bottom portion is proximal to the bottom edge of the back plate, and wherein the angled rack slopes away from the back plate in the direction from the top portion to the bottom portion at the selected angle; and
   c. a cover that is releasably attached to the back plate and is movable between an open position and a closed position relative to the back plate so as to allow access to the interior volume of the dispenser,
      wherein at least a portion of the opening through which the gloves may be dispensed is located through the cover and the opening through which gloves may be dispensed faces in a forward and downward direction relative to and away from the vertical surface.

31. The glove dispenser as claimed in claim 30, wherein the bottom portion of the angled rack further comprises at least one support for holding the prepackaged box of gloves and the central portion of the angled rack provides a resting surface for the prepackaged box of gloves.

32. The glove dispenser as claimed in claim 31, wherein the angle rack further comprises side portions for maintaining the prepackaged box of gloves in a certain position within the dispenser.

33. The glove dispenser as claimed in claim 31, further comprising top stays for preventing the prepackaged box of gloves from traveling upwards within the dispenser.

34. The glove dispenser as claimed in claim 31, wherein the cover further comprises a front wall comprising a bottom edge and a bottom wall comprising a front edge that intersect at a junction, and the opening through which gloves may be dispensed is located at the junction.

35. The glove dispenser as claimed in claim 34, wherein a first portion of the opening through which gloves may be dispensed is through the front wall and a second portion of the opening through which gloves may be dispensed is through the bottom wall.

36. The glove dispenser as claimed in claim 35, wherein the cover is hingedly attached to the back plate.

37. The glove dispenser as claimed in claim 35, wherein the cover is releasably attached to the back plate.

38. The glove dispenser as claimed in claim 35, wherein the front wall further comprises a window for viewing into the interior volume of the dispenser.

* * * * *